US012586665B2

(12) United States Patent
Oh et al.

(10) Patent No.: US 12,586,665 B2
(45) Date of Patent: Mar. 24, 2026

(54) APPARATUS FOR OBTAINING COLOR RAW MATERIAL FOR COSMETICS

(71) Applicant: LG HOUSEHOLD & HEALTH CARE LTD., Seoul (KR)

(72) Inventors: Se Heon Oh, Seoul (KR); Hye Jin Jeong, Seoul (KR); Chang Young Park, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 417 days.

(21) Appl. No.: 18/275,696

(22) PCT Filed: Dec. 17, 2021

(86) PCT No.: PCT/KR2021/019270
§ 371 (c)(1),
(2) Date: Aug. 3, 2023

(87) PCT Pub. No.: WO2022/169096
PCT Pub. Date: Aug. 11, 2022

(65) Prior Publication Data
US 2024/0112762 A1     Apr. 4, 2024

(30) Foreign Application Priority Data

Feb. 4, 2021     (KR) ........................ 10-2021-0016116
Mar. 19, 2021     (KR) ........................ 10-2021-0036223

(51) Int. Cl.
*G16C 20/30*     (2019.01)
*G16C 20/70*     (2019.01)

(52) U.S. Cl.
CPC ............. *G16C 20/30* (2019.02); *G16C 20/70* (2019.02)

(58) Field of Classification Search
CPC ......... G16C 20/70; G16C 60/00; G16C 20/30
See application file for complete search history.

(56) References Cited

U.S. PATENT DOCUMENTS

| | | | |
|---|---|---|---|
| 6,284,228 B1 | 9/2001 | Markowitz et al. | |
| 2014/0023231 A1* | 1/2014 | Iwamoto | ................ H04N 1/628 |
| | | | 382/165 |
| 2015/0245009 A1* | 8/2015 | Tozuka | ................ H04N 1/6086 |
| | | | 433/29 |

(Continued)

FOREIGN PATENT DOCUMENTS

| | | |
|---|---|---|
| CN | 107392166 A | 11/2017 |
| JP | 2010-536046 A | 11/2010 |

(Continued)

OTHER PUBLICATIONS

Draus et al., "Formulation of Colors Using a Genetic Algorithm", Image Processing & Communication, vol. 17, No. 4, 2012, pp. 241-244.

(Continued)

*Primary Examiner* — Sujoy K Kundu

(74) *Attorney, Agent, or Firm* — Birch, Stewart, Kolasch & Birch, LLP

(57) ABSTRACT
The present disclosure relates to an apparatus for obtaining a raw material which extracts a color raw material for cosmetics having a target color, wherein when a target color development value is input, raw material information is extracted using a genetic algorithm.

20 Claims, 11 Drawing Sheets

(56)            References Cited

U.S. PATENT DOCUMENTS

| | | |
|---|---|---|
| 2018/0310692 A1 | 11/2018 | Knuebel et al. |
| 2018/0360190 A1 | 12/2018 | Villalobos Lingoes et al. |
| 2019/0014884 A1* | 1/2019 | Fu ........................ G06T 1/0007 |
| 2019/0295728 A1 | 9/2019 | Jeong et al. |
| 2020/0410719 A1* | 12/2020 | Borkman .............. G06T 11/001 |
| 2021/0076807 A1 | 3/2021 | Pack et al. |
| 2021/0289923 A1 | 9/2021 | Jeong |
| 2021/0350174 A1* | 11/2021 | Merkle ..................... G06T 5/92 |

FOREIGN PATENT DOCUMENTS

| | | |
|---|---|---|
| JP | 2012-152598 A | 8/2012 |
| KR | 10-1936751 B1 | 4/2019 |
| KR | 10-2019-0050832 A | 5/2019 |
| KR | 10-2020-0017640 A | 2/2020 |
| WO | WO 2018/231915 A1 | 12/2018 |

OTHER PUBLICATIONS

Jang et al., "Spectrum-Based Color Reproduction Algorithm for Makeup Simulation of 30 Facial Avatar", ETRI Journal, vol. 35, No. 6, 2013, pp. 969-979.

* cited by examiner

FIG. 3

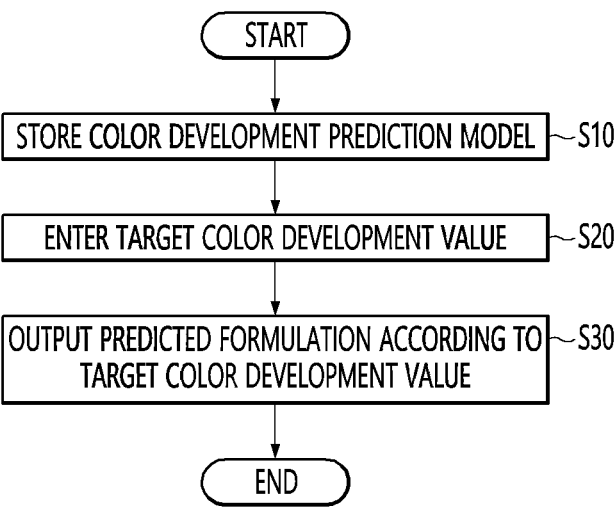

START

STORE COLOR DEVELOPMENT PREDICTION MODEL ~S10

ENTER TARGET COLOR DEVELOPMENT VALUE ~S20

OUTPUT PREDICTED FORMULATION ACCORDING TO
TARGET COLOR DEVELOPMENT VALUE ~S30

END

FIG. 4

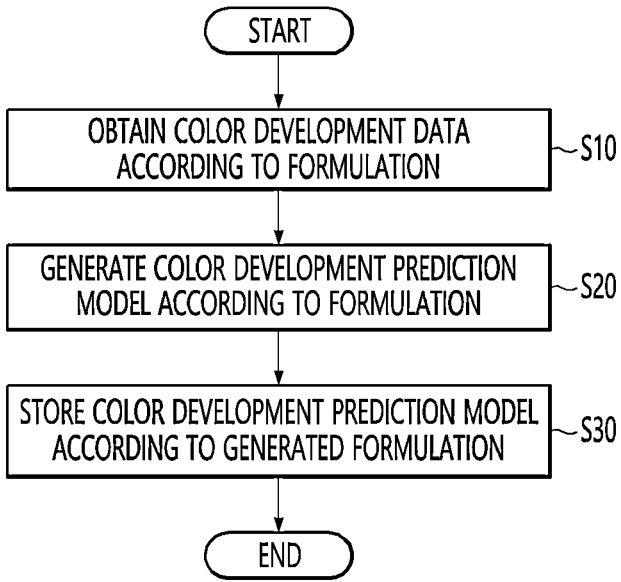

START

OBTAIN COLOR DEVELOPMENT DATA
ACCORDING TO FORMULATION ~S10

GENERATE COLOR DEVELOPMENT PREDICTION
MODEL ACCORDING TO FORMULATION ~S20

STORE COLOR DEVELOPMENT PREDICTION MODEL
ACCORDING TO GENERATED FORMULATION ~S30

END

1210

1220

1310

1320

APPARATUS FOR OBTAINING COLOR RAW MATERIAL FOR COSMETICS

CROSS REFERENCE TO RELATED APPLICATIONS

This application is the National Phase of PCT International Application No. PCT/KR2021/019270, filed on Dec. 17, 2021, which claims priority under 35 U.S.C. 119(a) to Patent Application No. 10-2021-0016116, filed in the Republic of Korea on Feb. 4, 2021 and Patent Application No. 10-2021-0036223, filed in the Republic of Korea on Mar. 19, 2021, all of which are hereby expressly incorporated by reference into the present application.

TECHNICAL FIELD

The present disclosure relates to an apparatus for obtaining a color raw material for cosmetics, and more particularly, for predicting a formulation of color ingredients for cosmetics using a genetic algorithm.

BACKGROUND ART

Among various cosmetic products, market needs in color cosmetics are changed very rapidly, and if new technologies can be introduced to improve research and development efficiency for new color products, it may be expected to obtain increased brand value and economic benefits through rapid response compared to competitors.

However, since a lot of time and experiments are required to develop a new color product, there is a problem that high cost should be invested in developing the new color product, but also it takes a long time.

DISCLOSURE

Technical Problem

The present disclosure is directed to providing an apparatus for obtaining a raw material for extracting a color raw material for cosmetics, a method of obtaining a raw material, and a system for obtaining a raw material.

The present disclosure is directed to minimizing time, cost, and effort in developing a new color product.

The present disclosure is directed to providing an apparatus for obtaining a raw material capable of formulating color raw material ingredients in cosmetics in consideration of limitations such as the maximum number of pigments, a range of content ratio for each pigment and a total content ratio of pigments used in the formulation.

The present disclosure is directed to providing an apparatus for obtaining a raw material, wherein colors may be developed very densely and almost unlimitedly through formulations of the raw material obtained by the apparatus.

Technical Solution

An apparatus for obtaining a raw material according to the present disclosure intends to replace a series of processes such as pigments formulating, experimentally color mixing and correcting required for new color development through machine learning.

In the apparatus for obtaining a raw material according to the present disclosure, option items such as the maximum number of pigments, a range of content ratio for each pigment, and a total content ratio of pigments used in the formulation can be set according to user needs.

An apparatus for obtaining a raw material according to the present disclosure may include an input unit for receiving a target color for development, a formulation sample group generation unit for generating a formulation sample group according to the target color for development, a formulation sample improvement unit for outputting the formulation sample group as an improved sample group using a genetic algorithm, and an output unit for outputting raw material information for manufacturing color cosmetics having the target color for development based on the improved sample group output from the formulation sample improvement unit.

The input unit may further receive an option item, and the formulation sample improvement unit may output the raw material information by reflecting the option item.

The option item may include at least one of the maximum number of raw materials to be used, a range of content ratio for each raw material, and a total raw material content.

The formulation sample improvement unit may include a sample candidate derivation unit for outputting a combination sample based on input existing samples, a sample evaluation unit for calculating the first color difference between a predicted color development of the existing sample and the target color for development and the second color difference between a predicted color development of the combination sample and the target color for development, and a sample selection unit for outputting the sample having the smaller value among the first and the second color differences as the improved sample in the improved sample group.

When there is an option item, the formulation sample improvement unit may compare the first color difference on which a penalty according to the option item is reflected with the second color difference on which a penalty according to the option item is reflected.

The apparatus for obtaining a raw material may further include a color development prediction calculation unit for calculating the predicted color development of the existing sample and the predicted color development of the combination sample through a regression model.

The sample candidate derivation unit may generate the combination sample by selecting any one of the existing samples and any one of the remaining existing samples as a random sample, mutating the random sample, and then combining the mutated sample with the selected existing sample.

The apparatus for obtaining a raw material may further include an improved sample group convergence checking unit that outputs the improved sample group to the formulation sample improvement unit or the output unit according to whether all samples in the improved sample group converges to a preset reference range.

An apparatus for obtaining a raw material according to an embodiment of the present disclosure may include a color development prediction model generation unit for generating a regression model providing color development data according to formulation data, and a color development prediction calculation unit for outputting a predicted color development value through the regression model when a predicted formulation is input, wherein the formulation data are color raw material information on cosmetics previously manufactured, and the color development data are the pre-measured color values of the color cosmetics.

The apparatus for obtaining a raw material may further include a predicted formulation generation unit configured to receive the target color for development, transmit a predicted formulation generated according to the target color for development to the color development prediction calculation unit, and receive the predicted color development value corresponding to the predicted formulation from the color development prediction calculation unit.

The predicted formulation generation unit may improve the predicted formulation until a color difference between the predicted color development value and the target color for development converges within a preset reference range.

The predicted formulation generation unit may improve the predicted formulation using a genetic algorithm.

Advantageous Effects

According to the present disclosure, since a color raw material information for manufacturing cosmetics having a specific color is output through a color development prediction model, there is an advantage that time, cost, and effort for manufacturing cosmetics with a new color can be minimized.

According to the present disclosure, since an option item to be applied for raw material formulation may be set according to user needs, there is an advantage that a color raw material for cosmetics can be formulated in consideration of realistic limitations.

According to the present disclosure, there is an advantage that color cosmetics with the desired colors may be manufactured unlimitedly.

DESCRIPTION OF DRAWINGS

FIG. 3 is a flowchart illustrating an operating method of an apparatus for obtaining a color raw material for cosmetics according to an embodiment of the present disclosure.

FIG. 4 is a flowchart illustrating a method for storing a color development prediction model by an apparatus for obtaining a raw material according to an embodiment of the present disclosure.

MODES OF THE PRESENT INVENTION

Figure 1:
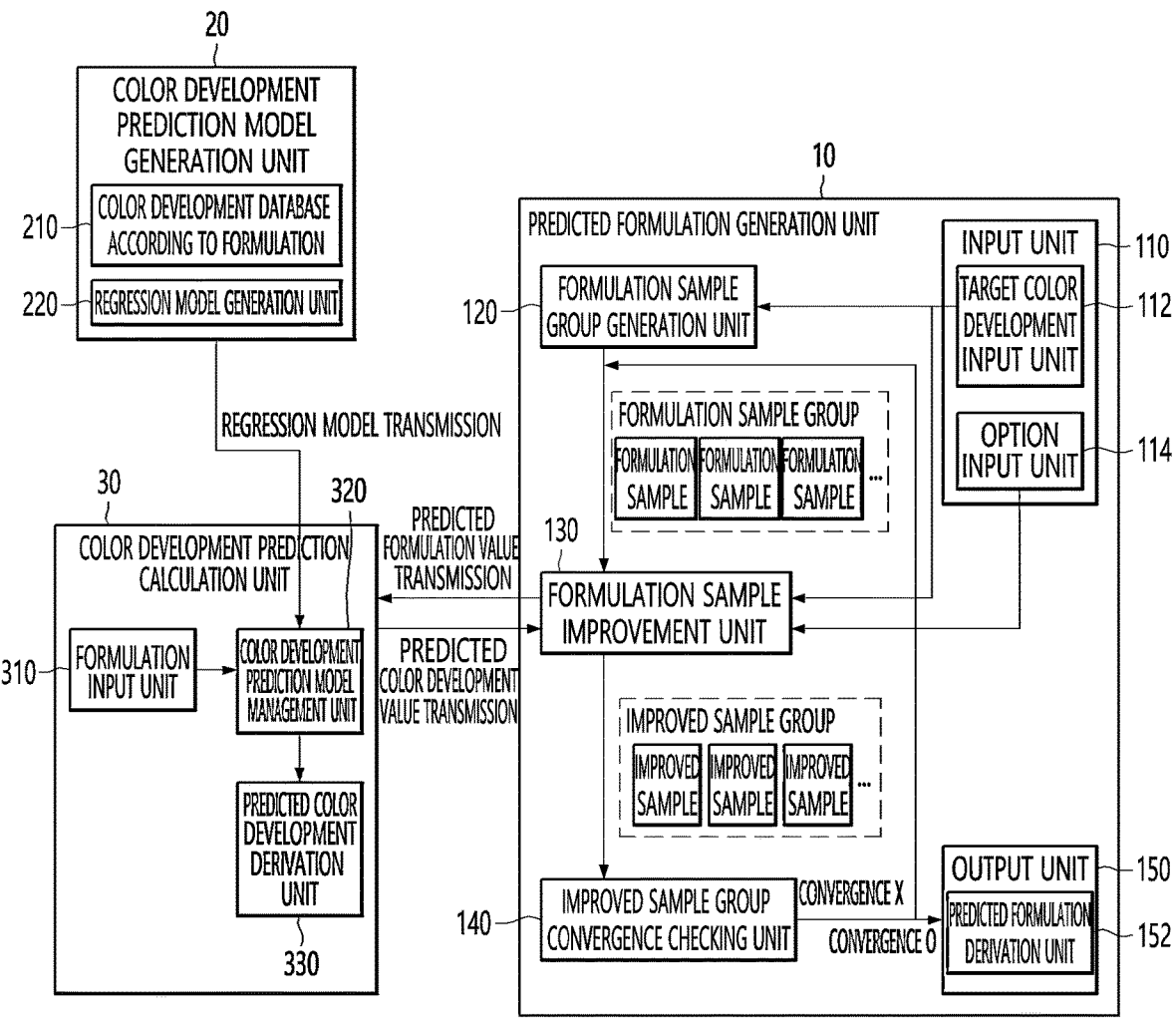
FIG. 1 is a control block diagram of an apparatus for obtaining a color raw material for cosmetics according to an embodiment of the present disclosure.

Hereinafter, embodiments will be described in detail with reference to the accompanying drawings, however, the same components are designated by the same reference numerals, and redundant description thereof will be omitted.

Suffixes "module" and "part" for elements used in the following descriptions are given or used just for convenience in writing the specification, and do not have meanings or roles distinguishable between them.

In addition, in describing embodiments of the present disclosure, when detailed description of a known function is deemed to unnecessarily blur the gist of the present disclosure, the detailed description will be omitted. Further, accompanying drawings are only for easily understanding embodiments disclosed in the present disclosure, and the technical spirit disclosed in the present disclosure are not limited by the accompanying drawings, and it should be understood that the present invention includes all modifications, equivalents, and alternatives falling within the spirit and scope of the claims.

It should be understood that, although the terms first, second, and the like may be used herein to describe various elements, these elements are not limited by these terms. The terms are only used to distinguish one element from another.

Elements referred to in singular may be number one or more, unless the context clearly indicates otherwise.

It should be further understood that the terms "comprises," "comprising," "includes," and/or "including," when used herein, specify the presence of stated features, integers, steps, operations, elements, components, and/or groups thereof, but do not preclude the presence or addition of one or more other features, integers, steps, operations, elements, components, and/or groups thereof.

FIG. 1 is a control block diagram of an apparatus for obtaining a color raw material for cosmetics according to an embodiment of the present disclosure.

The apparatus for obtaining a color raw material for cosmetics may include at least some or all of a predicted formulation generation unit 10, a color development prediction model generation unit 20, and a color development prediction calculation unit 30.

The predicted formulation generation unit 10 may receive a target color for development and output a predicted formulation. The predicted formulation generation unit 10 may be a configuration that outputs predicted formulation data for deriving the target color for development when receiving the target color for development and an option item (a formulation restriction) to be described later as an input value.

The target color for development may refer to the color expressed when a user uses color cosmetics.

The predicted formulation may refer to information on raw materials to be used for manufacturing color cosmetics having a target color for development.

In the present specification, a raw material may refer to an ingredient used for color development in color cosmetics. The raw material may include a pigment.

The predicted formulation generation unit 10 may include at least some or all of an input unit 110, the formulation sample group generation unit 120, the formulation sample improvement unit 130, the improved sample group convergence checking unit 140, and the output unit 150.

The input unit 110 may receive a target color for development. In addition, the input unit 110 may further receive an option item.

The target color for development may be an L*, a*, b* value of an internal color/external color. That is, the target color for development may be a total of six values: the internal color L*, a*, b* and the external color L*, a*, b*. However, this is merely illustrative, and the target color for development may have other forms.

The option item may refer to a restriction item to be reflected when outputting the predicted formulation. That is, the option item may be a formulation restriction item.

For example, the option item may include the maximum number of raw materials, a range of content ratio for each raw material, and a total raw material content, and the like, but these are merely illustrative and are not limited thereto. In addition, here, the raw material may refer to a pigment. In the present specification, depending on the case, the terms raw material and pigment may be interchangeably used.

The input unit 110 may include a target color input unit 112 for receiving the target color for development and an option input unit 114 for receiving the option item.

The target color for development input through the target color input unit 112 may be output to the formulation sample group generation unit 120 and the formulation sample improvement unit 130.

The formulation sample group generation unit 120 may generate a formulation sample group according to the target color for development.

Specifically, when the target color for development is input from the target color input unit 112, the formulation sample group generation unit 120 may generate the formulation sample group according to the received target color for development.

The formulation sample group generation unit 120 may randomly generate the formulation sample group.

The formulation sample group may include a plurality of formulation samples. A number of formulation samples in the formulation sample group may be determined through Equation 1 below.

$$\text{Nsample} = \text{Npigment} \times m\{m | m \geq 5\} \qquad \text{[Equation 1]}.$$

Nsample refers to the number of formulation samples in the formulation sample group, Npigment refers to the number of raw materials, and m may be 5 or more, but this is merely illustrative.

The formulation sample group generation unit 120 may generate formulation samples within the range of content ratio for each raw material when there is an option item for the range of content ratio for each raw material.

The formulation sample improvement unit 130 may receive the formulation sample group to derive an improved sample group. According to one embodiment, the formulation sample improvement unit 130 may derive the improved sample group using a genetic algorithm. When the formulation sample improvement unit 130 receives a formulation sample group, the formulation sample improvement unit 130 may output the improved sample group for the input formulation sample group.

The improved sample group may refer to an improved sample group such that each of the formulation samples in the formulation sample group is close to the predicted formulation for the target color for development. The improved sample group may consist of improved samples, wherein each of the formulation sample in the formulation sample group may be adjusted.

The formulation sample improvement unit 130 may output the formulation sample group as the improved sample group using the genetic algorithm. That is, the formulation sample improvement unit 130 may be configuration that applies the genetic algorithm, and when the formulation sample group is received as an input value, the formulation sample improvement unit 130 may perform a function of evolving the formulation sample group after comparing the predicted color development values obtained by transmitting the formulation samples to the color development prediction calculation unit 30. The formulation sample improvement unit 130 may finally converge all the formulation samples in the group to the formulations that may derive the predicted color development closest to the target color for development by performing this process until all the formulation samples in the group are similar. In this case, it may be desirable to converge the formulation samples in the group by additionally including a process of giving a penalty for the option item according to the present invention. For example, the formulation sample improvement unit 130 may converge the formulation samples in the group by giving a penalty according to the option item when deriving the predicted color development closest to the target color for development for all the formulation samples in the group.

When the target color for development is input, the predicted formulation generation unit 10 may transmit a predicted formulation value according to the target color for development to the color development prediction calculation unit 30 and receive a predicted color development value according to the predicted formulation value from the color development prediction calculation unit 30. The predicted formulation generation unit 10 may improve the predicted formulation value until a color difference between the predicted color development value and the target color for development converges within a preset reference range. The predicted formulation generation unit 10 may improve the predicted formulation value using a genetic algorithm.

The formulation sample improvement unit 130 may output raw material information for manufacturing color cosmetics having the target color for development. In addition, when there is an option item, the formulation sample improvement unit 130 may output the raw material information by reflecting the option item.

The improved sample group convergence checking unit 140 may check whether the improved sample group converges. The improved sample group convergence checking unit 140 may check whether the improved sample group converges by determining whether the improved samples in the improved sample group have converged to a preset reference range. The improved sample group convergence checking unit 140 may output the improved sample group to the formulation sample improvement unit 130 or the output unit 150 according to whether all samples in the improved sample group converge to the preset reference range.

According to one embodiment, when a variance of a predicted formulation contents $\{A_{n.0.1}, A_{n.1.1}, \ldots, A_{n.m.1}\}$ of the first raw material in the samples of the improved sample group is $m_a$, the improved sample group convergence checking unit 140 may determine that the improved samples in the improved sample group converge to the preset reference range if all variance $m_a$, $m_b$, $m_c$, ... for each of all raw materials are less than the preset reference value. Here, the preset reference value may be less than 0.1, but this is merely illustrative, and thus it is appropriate that the preset reference value is not limited thereto.

If the improved samples is determined to converge to the preset reference range, the improved sample group convergence checking unit 140 may determine that the improved sample group converges thereto, and if the improved samples is determined to not converge to the preset reference range, the improved sample group convergence checking unit 140 may determine that the improved sample group does not converges thereto.

When the improved sample group does not converge to the preset reference range, the improved sample group convergence checking unit 140 may output the improved sample group as the formulation sample group, returning to the formulation sample improvement unit 130. That is, the improved sample group determined to not converge thereto in the improved sample group convergence checking unit 140 may be fed back to the formulation sample improvement unit 130 as the formulation sample group.

Accordingly, the formulation sample improvement unit 130 may output a further improved sample group with respect to the input improved sample group. The formulation sample improvement unit 130 may recognize the input improved sample group as the formulation sample group. In this way, the formulation sample improvement unit 130 may output an N-th sample group as an N+1th sample group.

When the improved sample group converges to the preset reference range, the improved sample group convergence checking unit 140 may transmit the improved sample group to the output unit 150.

The output unit 150 may output raw material information for manufacturing color cosmetics having a target color for development based on the improved sample group output from the formulation sample improvement unit, where the raw material information may include a content ratio for each raw material. The output unit 150 may output the improved sample group input from the improved sample group convergence checking unit 140 as a predicted formulation. Based on the improved sample group input from the improved sample group convergence checking unit 140, the output unit 150 may output the raw material information for manufacturing color cosmetics having a target color for development. That is, the predicted formulation (the result formulation) may include raw material information for manufacturing color cosmetics having a target color for development. The output unit 150 may include a predicted formulation derivation unit 152 that outputs the predicted formulation.

Meanwhile, the formulation sample improvement unit 130 may derive the formulation sample group as the improved sample group through the color development prediction calculation unit 30.

The color development prediction calculation unit 30 may calculate a predicted color development of an existing sample and a predicted color development of a combination sample through a regression model.

Specifically, the formulation sample improvement unit 130 may transmit a predicted formulation according to the input formulation sample group to the color development prediction calculation unit 30. The color development prediction calculation unit 30 may output a predicted color development value of the predicted formulation input from the formulation sample improvement unit 130 to the formulation sample improvement unit 130. The formulation sample improvement unit 130 may output the improved sample group with reference to the predicted color development value input from the color development prediction calculation unit 30.

The color development prediction calculation unit 30 may be a configuration in which a color development prediction model generated by the color development prediction model generation unit 20 calculates an actual color development prediction. The color development prediction calculation unit 30 may output an expected color development value (external color development value, internal color development value) when receiving arbitrary raw material formulation data as an input value.

The color development prediction calculation unit 30 may include at least some or all of a formulation input unit 310, a color development prediction model management unit 320, and a predicted color development derivation unit 330.

The formulation input unit 310 may receive a predicted formulation value from the predicted formulation generation unit 10, in particular, the formulation sample improvement unit 130.

The formulation input unit 310 may output the received predicted formulation value to the color development prediction model management unit 320.

The color development prediction model management unit 320 may store a color development prediction model. The color development prediction model may include a color development regression model according to a formulation.

The color development prediction model management unit 320 may input the predicted formulation value to the color development prediction model and output an output from the color development prediction model to the predicted color development derivation unit 330. The predicted color development derivation unit 330 may transmit the output which is input from the color development prediction model management unit 320 as the predicted color development value to the predicted formulation generation unit 10, in particular the formulation sample improvement unit 130.

In this way, the formulation sample improvement unit 130 may obtain the predicted color development value for the predicted formulation value through the color development prediction model management unit 320, improve the formulation samples in the formulation sample group by referring thereto, and output the improved sample group.

Meanwhile, the regression model stored in the color development prediction model management unit 320 may be input from the color development prediction model generation unit 20.

The color development prediction model generation unit 20 may generate a regression model by using matching information between color development data and formulation data. Here, the formulation data may be color raw material information on cosmetics previously manufactured, and the color development data may include the color values (e.g., L*, a*, and b* for each of the internal and external colors) of the color cosmetics.

The color development prediction model generation unit 20 may include at least some or all of a database 210 and a regression model generation unit 220.

The database 210 may store the color development data for the formulation data. The formulation data may include a content ratio for each raw material, and the color development data may include L*, a*, and b* for each of the internal and external colors. That is, the database 210 may include L*, a*, and b* values of the internal color and the external color for the content ratio of each raw material.

The formulation data stored in the database 210 may include a type of a base formulation and a composition of a color development raw material. Here, the base formulation refers to a composition of a raw material excluding color raw materials involved in color development among the entire formulation for manufacturing final color cosmetics, and the regression model may be separately generated through the regression model generation unit 220 for each type of the base formulation. This may be necessary to minimize the effect of the base formulation on the predicted formulation obtained through the apparatus for obtaining a color raw material according to the present invention. In this case, the apparatus for obtaining a color raw material according to the present invention may select the type of the base formulation together with the target color for development as an input value, and the predicted formulation as the result value may include the type of the base formulation or the composition of the base formulation and the composition of the predicted color development raw material.

The regression model generation unit 220 may generate a regression model providing a color development according to a formulation. That is, the regression model generation unit 220 may generate the regression model using the color development data according to the formulation data stored in the database 210. The regression model may be a multiple regression model. The regression model may be a linear method or a non-linear method for predicting a result vector (Y) having a tendency from a plurality of vectors (X).

The regression model generation unit 220 may transmit the generated multiple regression model to the color prediction calculation unit 30, in particular, the color development prediction model management unit 320.

In summary, the color development prediction model generation unit 20 may be a configuration that generates a color development prediction model based on the color development value as experimental data measured for the raw material formulation. The color development prediction model may be a model that outputs an expected color development value (external color development value, internal color development value) when input arbitrary raw material formulation data as an input value. As the number of experimental data and a color region to be included are wider and denser, the color development prediction model generation unit 20 may generate a color development prediction model with high accuracy.

Next, an operation method of the formulation sample improvement unit 130 will be described in more detail with reference to FIG. 2. The operation method of the formulation sample improvement unit 130, as described later, may be the operation method using a genetic algorithm.

Figure 2:
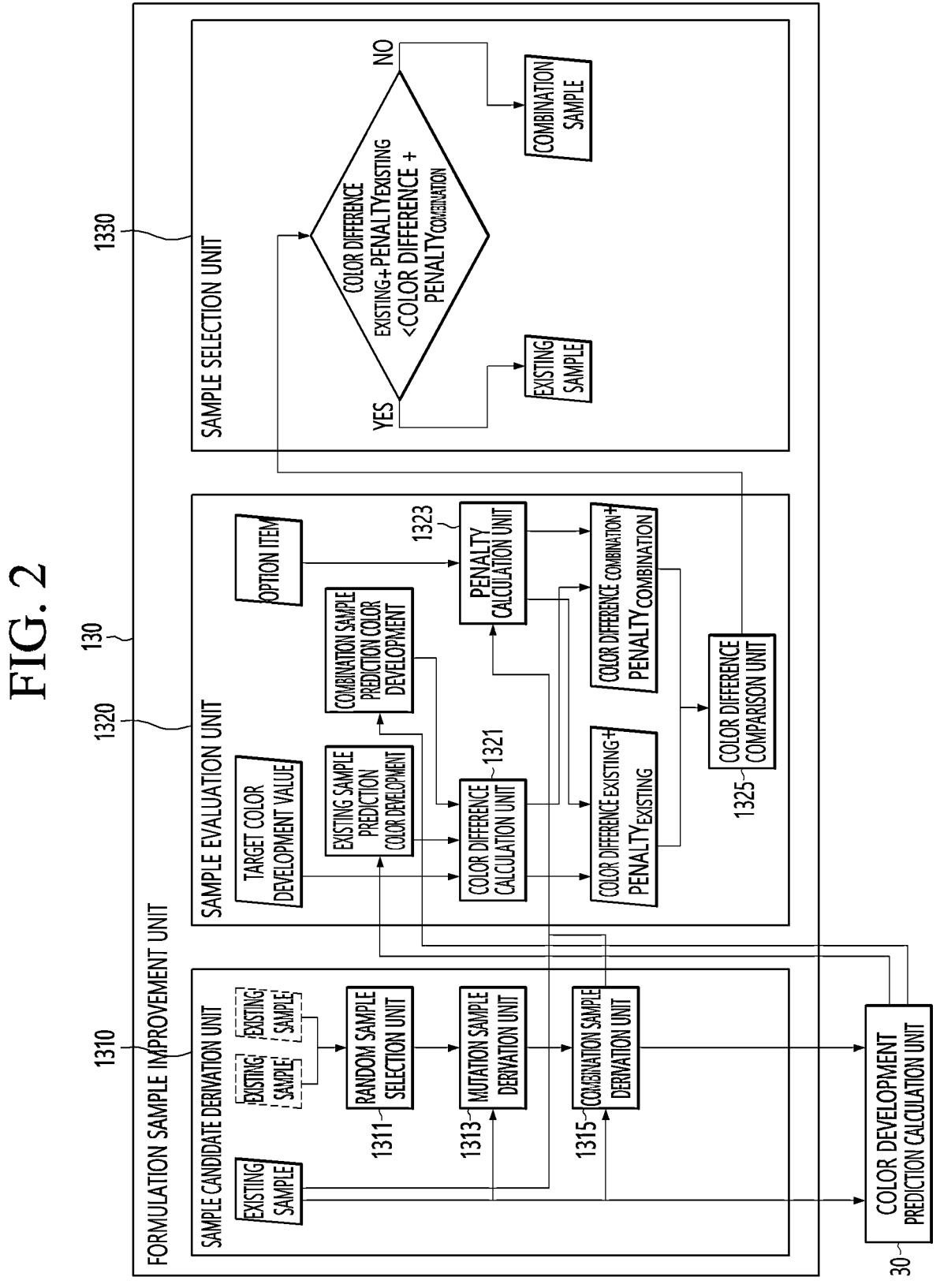
FIG. 2 is a control block diagram of a formulation sample improvement unit according to an embodiment of the present disclosure.

FIG. 2 is a control block diagram of a formulation sample improvement unit according to an embodiment of the present disclosure.

The formulation sample improvement unit 130 may include at least some or all of a sample candidate derivation unit 1310, a sample evaluation unit 1320, and a sample selection unit 1330.

The sample candidate derivation unit 1310 may output a sample candidate that may be an improved sample. The sample candidate derivation unit 1310 may output a combination sample based on a received existing sample. The sample candidate derivation unit 1310 may generate the combination sample by the following: selecting any one of the existing samples and any one of the remaining existing samples as a random sample, mutating the random sample, and then combining the mutated random sample with the selected existing sample. A method for generating the combination sample will be described in detail below.

The sample candidate derivation unit 1310 may derive the combination sample by the following: generating a random sample, generating a mutation sample by interpolating the existing sample and the random sample, and probabilistically selecting and combining the existing sample and the mutation sample. To this end, the sample candidate derivation unit 1310 may include a random sample selection unit 1311 configured to randomly select one of the existing samples, a mutation sample derivation unit 1313 configured to generate the mutation sample, and a combination sample derivation unit 1315 configured to generate the combination sample. Here, the existing sample may be a formulation sample input from the formulation sample improvement unit 130.

Meanwhile, the generated combination sample may be output to the color development prediction calculation unit 30 together with the existing sample. The color development prediction calculation unit 30 may calculate the predicted color development of the existing sample and the predicted color development of the combination sample and output them to the sample evaluation unit 1320.

The sample evaluation unit 1320 may calculate the first color difference between a predicted color development of the existing sample and the target color for development and the second color difference between a predicted color development of the combination sample and the target color for development. When there is an option item, the sample evaluation unit 1320 may compare the first color difference on which a penalty according to the option item is reflected with the second color difference on which a penalty according to the option item is reflected The sample evaluation unit 1320 may compare the predicted color development of the existing sample with the predicted color development of the combination sample.

The sample evaluation unit 1320 may include a color difference calculation unit 1321 and a color difference comparison unit 1325. The color difference calculation unit 1321 may receive the target color for development, the predicted color development of the existing sample, and the predicted color development of the combination sample and may calculate the first color difference between the target color for development and the predicted color development of the existing sample and the second color difference between the target color for development and the predicted color development of the combination sample.

The color difference comparison unit 1325 may compare the first color difference with the second color difference. The first color difference (color difference $_{existing}$) may be a color difference between the target color for development and the predicted color development of the existing sample, and the second color difference (color difference $_{combination}$) may refer to a color difference between the target color for development and the predicted color development of the combination sample.

The color difference comparison unit 1325 may output a comparison result of the first color difference and the second color difference to the sample selection unit 1330.

The sample selection unit 1330 may output the sample having the smaller value among the first and second color differences as the improved sample in the improved sample group.

When the first color difference is the smaller than the second color difference, the sample selection unit 1330 may output the existing sample as the improved sample, and when the first color difference is the greater than the second color difference, the sample selection unit 1330 may output the combination sample as the improved sample.

That is, the sample selection unit 1330 may output the sample having the smaller color difference from the target color for development as the improved sample.

Meanwhile, the sample evaluation unit 1320 may further include a penalty calculation unit 1323.

The penalty calculation unit 1323 may receive an existing sample, a combination sample, and an option item.

The penalty calculation unit 1323 may calculate a first penalty reflected color difference and a second penalty reflected color difference when there is an option item. The first penalty reflected color difference (color difference $_{existing}$+penalty $_{existing}$) may be the sum of the first color difference and the first penalty according of the existing sample, and the second penalty reflected color difference (color difference $_{combination}$+penalty $_{combination}$) may be the sum of the second color difference and the second penalty of the combination sample.

In this case, the color difference comparison unit 1325 may compare the first penalty reflected color difference with the second penalty reflected color difference, and may output the comparison result to the sample selection unit 1330.

The sample selection unit 1330 may output the existing sample as the improved sample when the first penalty reflected color difference is the smaller than the second penalty reflected color difference and may output the combination sample as the improved sample when the first penalty reflected color difference is the greater than the second penalty reflected color difference.

As described above, the improved sample derived by the formulation sample improvement unit 130 may be input to the formulation sample improvement unit 130 again or may be input to the output unit 150 after going through the improved sample group convergence checking unit 140.

Through the above-described method, the predicted formulation generation unit 10 may create a function for calculating the color difference and a function for calculating the penalty for the option item, apply the genetic algorithm, and induce the result at which the values of the two functions converge to 0, resulting in an optimal predicted formulation.

FIG. 3 is the flowchart illustrating an operating method of an apparatus for obtaining a color raw material for cosmetics according to an embodiment of the present disclosure.

Referring to FIG. 3, the apparatus for obtaining a raw material may store a color development prediction model (S10).

Next, a method in which the apparatus for obtaining a raw material stores the color development prediction model will be described in more detail with reference to FIG. 4. That is, with reference to FIG. 4, the step S10 in FIG. 3 will be described in detail.

FIG. 4 is the flowchart illustrating a method for storing a color development prediction model by an apparatus for obtaining a raw material according to an embodiment of the present disclosure.

The color development prediction model generation unit 20 may receive color development data according to a formulation (S10).

The color development data according to the formulation may be data including a color development value according to a content ratio of a raw material. Specifically, the color development data according to the formulation may include the first color development values according to a content ratio of a first raw material, the second color development values according to a content ratio of a second raw material, . . . , and an n-th color development value according to a content ratio of an n-th raw material. The color development values may refer to L*, a*, and b* values of each of internal and external colors of cosmetics.

The internal color may refer to the color developed by using cosmetics, and the external color may refer to the color of cosmetics itself before use.

The color development prediction model generation unit 20 may collect a large amount of color development data according to the formulation and update the data additionally.

The color development prediction model generation unit 20 may generate a color development prediction model according to the formulation based on the received color development data according to the formulation (S20).

The color development prediction model generation unit 20 may generate a color development prediction model according to the formulation by using the collected color development data according to the formulation. The color development prediction model according to the formulation may be a deep neural network (DNN) model. The DNN model may be the model that outputs a predicted color development value when the content ratio for each raw material is input.

The color development prediction model generation unit 20 may store the generated color development prediction model according to the formulation (S30).

Again, FIG. 3 will be described.

The apparatus for obtaining a raw material may receive a target color for development (S20).

For example, the apparatus for obtaining a raw material may receive the internal color L*, a*, b* and the external color L*, a*, b* as the target color for development.

Meanwhile, the apparatus for obtaining a raw material may further receive an option item along with the target color for development.

For example, the option item may include at least one of the maximum number of raw materials, a range of content ratio for each raw material, and a total raw material content ratio as used in the formulation.

The apparatus for obtaining a raw material may output a predicted formulation according to the input target color for development (S30).

Figure 5:
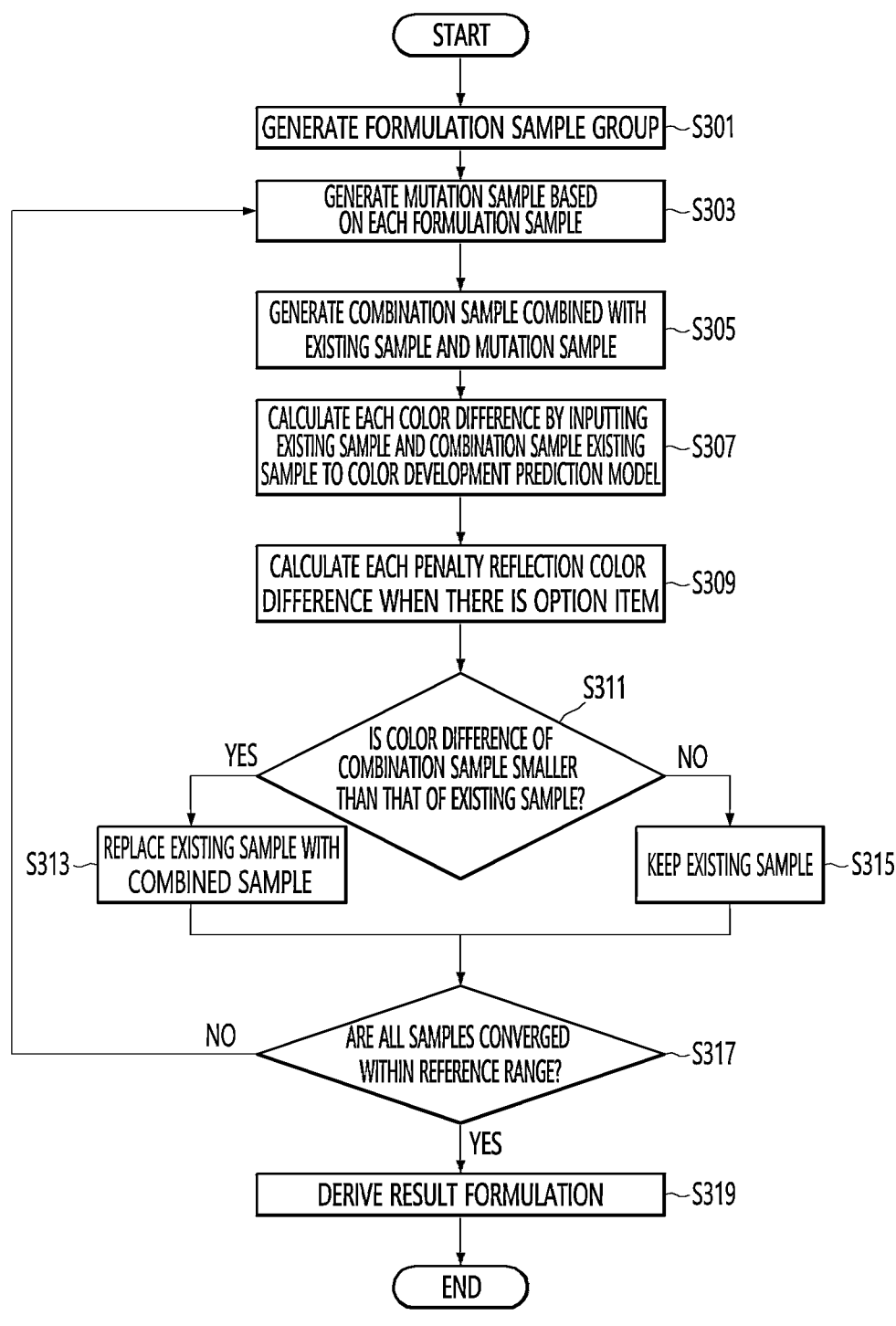
FIG. 5 is a flowchart illustrating a method for outputting, by an apparatus for obtaining a raw material according to an embodiment of the present disclosure, a predicted formulation according to a target color for development.

Next, a method for outputting, by the apparatus for obtaining a raw material, a predicted formulation according to a target color for development will be described with reference to FIG. 5. FIG. 5 is the flowchart in which the step S30 of FIG. 3 is embodied.

FIG. 5 is the flowchart illustrating a method of outputting, by an apparatus for obtaining a raw material according to an embodiment of the present disclosure, a predicted formulation according to a target color for development.

The formulation sample group generation unit 120 may generate a formulation sample group (S301).

The formulation sample group generation unit 120 may generate a formulation sample group when receiving a target color for development.

The formulation sample group may be $G_0$, $G_1$, $G_2$, $G_3$, . . . , $G_n$, $G_0$ is an initial formulation sample group, $G_1$ is the first improved sample group (the first-generation improved sample group), and $G_2$ is the second improved sample group (the second-generation improved sample group)), $G_3$ may be the third improved sample group (the third-generation improved sample group), . . . , $G_n$ may be an n-th improved sample group (an n-th-generation improved sample group).

The initial formulation sample group $G_0$ and the n-th improved sample group $G_n$ may be as follows.

$$G_0=\{S_{0.0},S_{0.1},S_{0.2}, \ldots ,S_{0.m}\}, G_n=\{S_{n.0},S_{n.1},S_{n.2}, \ldots ,S_{n.m}\}$$

Here, each of $S_{0.0}$, $S_{0.1}$, $S_{0.2}$, . . . , $S_{0.m}$ may represent one formulation sample. $S_{n.m}$ may represent the m-th sample of an n-th generation.

In addition, $S_{0.0}=\{A_{0.0.1}, A_{0.0.2}, A_{0.0.3}, \ldots \}$, $S_{0.1}=\{A_{0.1.1}, A_{0.1.2}, A_{0.1.3}, \ldots \}$, . . . , $S_{n.m}\{A_{n.m.1}, A_{n.m.2}, A_{n.m.3}, \ldots , A_{n.m.1}\}$, wherein each element constituting each formulation sample may represent a content of a raw material ingredient, the number of elements may be the same as the number of raw material ingredients to be formulated. That is, $A_{n.m.1}$ may refer to a content of the first pigment of m-th sample in n-th-generation.

The formulation sample improvement unit 130 may generate a mutation sample based on each formulation sample (S303) and generate a combination sample in which the existing sample and the mutation sample are combined (S305).

Here, the combination sample may also represent the combination sample generated based on the formulation sample input by the formulation sample improvement unit 130.

When the formulation sample improvement unit 130 receives the initial formulation sample group $G_0$, the formulation sample improvement unit 130 may firstly select any one of other existing samples $S_{0.1}$, $S_{0.2}$, . . . , $S_{0.m}$ in order to improve the existing sample $S_{0.0}$. For example, it is assumed that the formulation sample improvement unit 130 selects $S_{0.2}$ among other existing samples.

The formulation sample improvement unit 130 may perform interpolation on the two formulation samples $S_{0.0}$ and $S_{0.2}$. For example, when $S_{0.0}=\{0, 1, 3, 5\}$ and $S_{0.2}=\{1, 4, 6, 8\}$, as a result of selecting any one of the values between 0 and 1 of the first element, selecting any one of the values between 1 and 4 of the second element, selecting any one of the values between 3 and 6 of the third element, and selecting any one of the values between 5 and 8 of the fourth element, the formulation sample improvement unit 130 may generate the mutation sample such as $S_{0.0\ mutation}=\{0.5, 2, 5, 7\}$. That is, the formulation sample improvement unit 130 may generate the mutation sample for the existing sample $S_{0.0}$, which is $S_{0.0\ mutation}=\{$any value chosen between $A_{0.0.1}$ and $A_{0.2.1}$, any value chosen between $A_{0.0.2}$ and $A_{0.2.2}$, any value chosen between $A_{0.0.3}$ and $A_{0.2.3}$, . . . $\}$.

In addition, the formulation sample improvement unit 130 may generate $S_{0.0\ combination}=\{A_{0.0.1\ combination}, A_{0.0.2\ combination}, A_{0.0.3\ combination}, . . . \}$ as the result of randomly selecting any one value of the existing sample $S_{0.0}=\{A_{0.0.1}, A_{0.0.2}, A_{0.0.3}, . . . \}$ and the mutation sample $S_{0.0\ mutation}=\{A_{0.0.1\ mutation}, A_{0.0.2\ mutation}, A_{0.0.3\ mutation}, . . . \}$, which is $S_{0.0\ combination}=\{$any one of $A_{0.0.1}$ and $A_{0.0.1\ mutation}$, any one of $A_{0.0.2}$ and $A_{0.0.2\ mutation}$, any one of $A_{0.0.3}$ and $A_{0.0.3\ mutation}$, . . . $\}$. In the above example, when $S_{0.0}=\{0, 1, 3, 5\}$ and $S_{0.0\ mutation}=\{0.5, 2, 5, 7\}$, it may be $S_{0.0\ combination}=\{0.5, 2, 3, 5\}$, but this is merely illustrative, and thus this is not limited thereto.

Meanwhile, although the method for generating the combination sample for $S_{0.0}$ has been described as an example, the formulation sample improvement unit 130 may generate the combination sample for each of $S_{0.1}$, $S_{0.2}$, . . . , $S_{0.m}$ by applying the above-described method.

In summary, when $S_{n.m.r}$ is the random sample of the m-th sample in the n-th generation, the random sample may be, as selected by the formulation sample improvement unit 130, any one of other samples other than $S_{n.m}$ among samples constituting a $G_n$ sample group. That is, $S_{n.m.r}=\{A_{n.m.1.r}, A_{n.m.2.r}, A_{n.m.3.r}, . . . , A_{n.m.1.r}\}$, where $A_{n.m.1.r}$ may refer to a content of the l-th raw material of the random sample for the m-th sample in the n-th generation. $S_{n.m.mutation}$ is the mutation sample of the m-th sample in the n-th generation which is $S_{n.m.mutation}=\{A_{n.m.1.mutation}, A_{n.m.2.mutation}, A_{n.m.3.mutation}, . . . , A_{n.m.1.mutation}\}$, here $A_{n.m.1.mutation}$ may be any value chosen between $A_{n.m.1.}$ and $A_{n.m.1.r}$.

When the $S_{n.m.combination}$ is the combination sample of the m-th sample in the n-th generation, $S_{n.m.combination}=\{A_{n.m.1.combination}, A_{n.m.2.combination}, A_{n.m.3.combination}, . . . , A_{n.m.1.combination}\}$, and $A_{n.m.1.combination}$ may be one of $A_{n.m.1.}$ and $A_{n.m.1.mutation}$, and one of $A_{n.m.1.}$ and $A_{n.m.1.mutation}$ may be randomly selected for each raw material.

In addition, the formulation sample improvement unit 130 may calculate each color difference by inputting the existing sample and the combination sample to the color development prediction model (S307). When there is an option item, the formulation sample improvement unit 130 may calculate a penalty reflected color difference for each of the existing sample and the combination sample (S309).

The color difference may be calculated through Equation 2 below, and the penalty may be calculated through Equation 3 below.

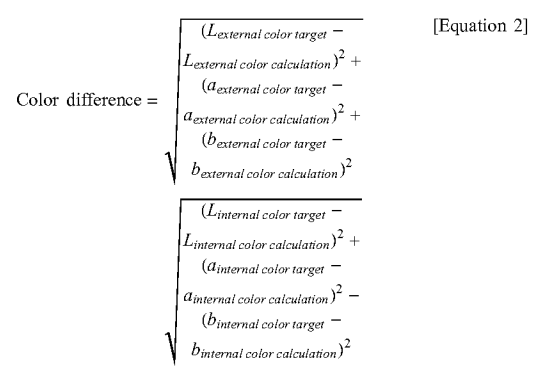

$$\text{Color difference} = \begin{cases} (L_{external\ color\ target} - \\ L_{external\ color\ calculation})^2 + \\ (a_{external\ color\ target} - \\ a_{external\ color\ calculation})^2 + \\ (b_{external\ color\ target} - \\ b_{external\ color\ calculation})^2 \end{cases} \quad \text{[Equation 2]}$$

$$\begin{cases} (L_{internal\ color\ target} - \\ L_{internal\ color\ calculation})^2 + \\ (a_{internal\ color\ target} - \\ a_{internal\ color\ calculation})^2 - \\ (b_{internal\ color\ target} - \\ b_{internal\ color\ calculation})^2 \end{cases}$$

Penalty =                       [Equation 3]

(Penalty constant value exceeding maximum number of pigments) +

(Panalty constant value exceeding total pigment content) +

(Panalty constant value exceeding content for each pigment)

In Equation 2, $L_{external\ color\ target}$ may represent an external color L* received as a target input value, $L_{external\ color\ calculation}$ may represent an external color L* of the predicted color development value calculated through the color prediction calculation unit 30, $a_{external\ color\ target}$ may represent an external color a* received as a target input value, $a_{external\ color\ calculation}$ may represent an external color a* of the predicted color development value calculated through the color prediction calculation unit 30, $b_{external\ color\ target}$ may represent an external color b* received as a target input value, and $b_{external\ color\ calculation}$ may represent an external color b* of the predicted color development value calculated through the color prediction calculation unit 30. $L_{internal\ color\ target}$ may represent an internal color L* received as a target input value, $L_{internal\ color\ calculation}$ may represent an internal color L* of the predicted color development value calculated through the color prediction calculation unit 30, $a_{internal\ color\ target}$ may represent an internal color a* received as a target input value, $a_{internal\ color\ calculation}$ may represent an internal color a* of the predicted color development value calculated through the color prediction calculation unit 30, $b_{internal\ color\ target}$ may represent an internal color b* received as a target input value, and $b_{internal\ color\ calculation}$ may represent an internal color b* of the predicted color development value calculated through the color prediction calculation unit 30.

The formulation sample improvement unit 130 may compare a color difference (color difference $_{combination}$) of the combination sample with a color difference (color difference $_{existing}$) of the existing sample. When there is an option item, the formulation sample improvement unit 130 may compare a penalty reflected color difference (color difference $_{combination}$+penalty $_{combination}$) for the combination sample with a penalty reflected color difference (color difference $_{existing}$+penalty $_{existing}$) for the existing sample.

Hereinafter, it is assumed that the meaning of the color difference (color difference $_{combination}$) for the combination sample includes the penalty reflected color difference (color difference $_{combination}$+penalty $_{combination}$) for the combination sample, and the meaning of the color difference (color difference $_{existing}$) for the existing sample includes the penalty reflected color difference (color difference $_{existing}$+penalty $_{existing}$) for the existing sample.

The formulation sample improvement unit 130 may obtain whether the color difference of the combination sample is smaller than the color difference of the existing sample (S311).

When the color difference of the combination sample is smaller than the color difference of the existing sample, the formulation sample improvement unit 130 may replace the existing sample with the combination sample (S313).

Accordingly, the formulation sample improvement unit 130 may output an improved sample group $G_1$ in which the combination sample included as an output for the input initial formulation sample group $G_0$.

When the color difference of the combination sample is greater than the color difference of the existing sample, the formulation sample improvement unit 130 may maintain the existing sample (S315).

Accordingly, the formulation sample improvement unit 130 may output an improved sample group $G_1$ in which the existing sample is included as an output for the input initial formulation sample group $G_0$.

The improved sample group convergence checking unit 140 may obtain whether all samples in the improved sample group output from the formulation sample improvement unit 130 converge within a reference range (S317).

Hereinafter, it is assumed that the improved sample group $G_n$ is input to the improved sample group convergence checking unit 140. In the improved samples $S_{n.0}$, $S_{n.1}$, $S_{n.2}$, ..., $S_{n.m}$ in the improved sample group $G_n=\{S_{n.0}, S_{n.1}, S_{n.2}, \ldots, S_{n.m}\}$, when variation of a content $\{A_{n.0.1}, A_{n.1.1}, \ldots, A_{n.m.1}\}$ of the first raw material is $m_a$, variation of a content $\{A_{n.0.2}, A_{n.1.2}, \ldots, A_{n.m.2}\}$ of the second raw material is $m_b$, variation of a content $\{A_{n.0.3}, A_{n.1.3}, \ldots, A_{n.m.3}\}$ of the third raw material is mc, . . . , and when all the variation $m_a$, $m_b$, $m_c$ , . . . for each raw material are less than the preset reference value, it may be determined that the improved samples in the improved sample group converge to the preset reference range. Here, the preset reference value may be less than 0.1, but this is merely illustrative, and thus it is appropriate that the preset reference value is not limited thereto.

When the improved sample group does not converge to the preset reference range, the improved sample group convergence checking unit 140 may input the improved sample group to the formulation sample improvement unit 130. Accordingly, the formulation sample improvement unit 130 may recognize the improved samples in the input improved sample group as the formulation samples, and generate a mutation sample based on each the formulation sample again.

As such, the formulation sample improvement unit 130 may recognize the input sample group as the formulation sample group, improve the recognized formulation sample group, and output as the improved sample group. Accordingly, the formulation sample improvement unit 130 may output the first improved sample group $G_1$ when the initial formulation sample group $G_0$ is input, output the second improved sample group $G_2$ when the first improved sample group $G_1$ is input, . . . , and output the n-th improved sample group $G_n$.

The first improved sample group $G_1$, . . . the n-th improved group sample group $G_n$ may be as follows.

$$G_1=\{S_{1.0}, S_{1.1}, S1_{n.2}, \quad . \quad . \quad . \quad , S_{1.m}\}, G_n=\{S_{n.0}, S_{n.1}, S_{n.2}, \ldots, S_{n.m}\}$$

Each of $S_{1.0}$, $S_{1.1}$, $S1_{n.2}$, . . . , $S_{1.m}$, . . . , $S_{n.0}$, $S_{n.1}$, $S_{n.2}$, . . . , $S_{n.m}$ may represent one formulation sample. In addition, it may be configured to $S_{1.0}=\{A_{1.0.1}, A_{1.0.2}, A_{1.0.3}, \ldots\}$, $S_{1.1}=\{A_{1.1.1}, A_{1.1.2}, A_{1.1.3}, \ldots\}$, . . . , $S_{n.m}=\{A_{n.m.1}, A_{n.m.2}, A_{n.m.3}, \ldots\}$, where each element constituting each formulation sample may represent a content of raw material ingredient, and the number of elements may be the same as the number of raw material ingredients to be formulated.

When all the samples in the improved sample group converge within the reference range, the improved sample group convergence checking unit 140 may derive result formulations (S319).

Specifically, when all the samples of the improved sample group converge within the reference range, the improved sample group convergence checking unit 140 may output the improved sample group to the output unit 150, and the output unit 150 may output the improved samples in the improved sample group as the result formulations.

FIGS. 6 to 11 are the diagrams illustrating examples for outputting result formulations according to a target color for development by an apparatus for obtaining a raw material according to an embodiment of the present disclosure.

More specifically, FIGS. 6 to 11 are examples illustrating the experimental results of confirming the performance of the apparatus for obtaining a raw material using cosmetics actually sold in the market where kinds of formulations and pigments are unknown. FIGS. 6 to 11 are the diagrams illustrating the result formulations and the colors according to the result formulations as output by the apparatus for obtaining a raw material after receiving external and internal colors for each of the cosmetics actually sold in the market as the target colors for development. In the experiments of FIGS. 6 to 11, the option item is set such that the total number of raw materials is 6 or less, a content ratio of black pigment is 0.5% or less in a range of content ratio for each pigment, and a total content ratio of used pigments is 20%.

Figure 6:
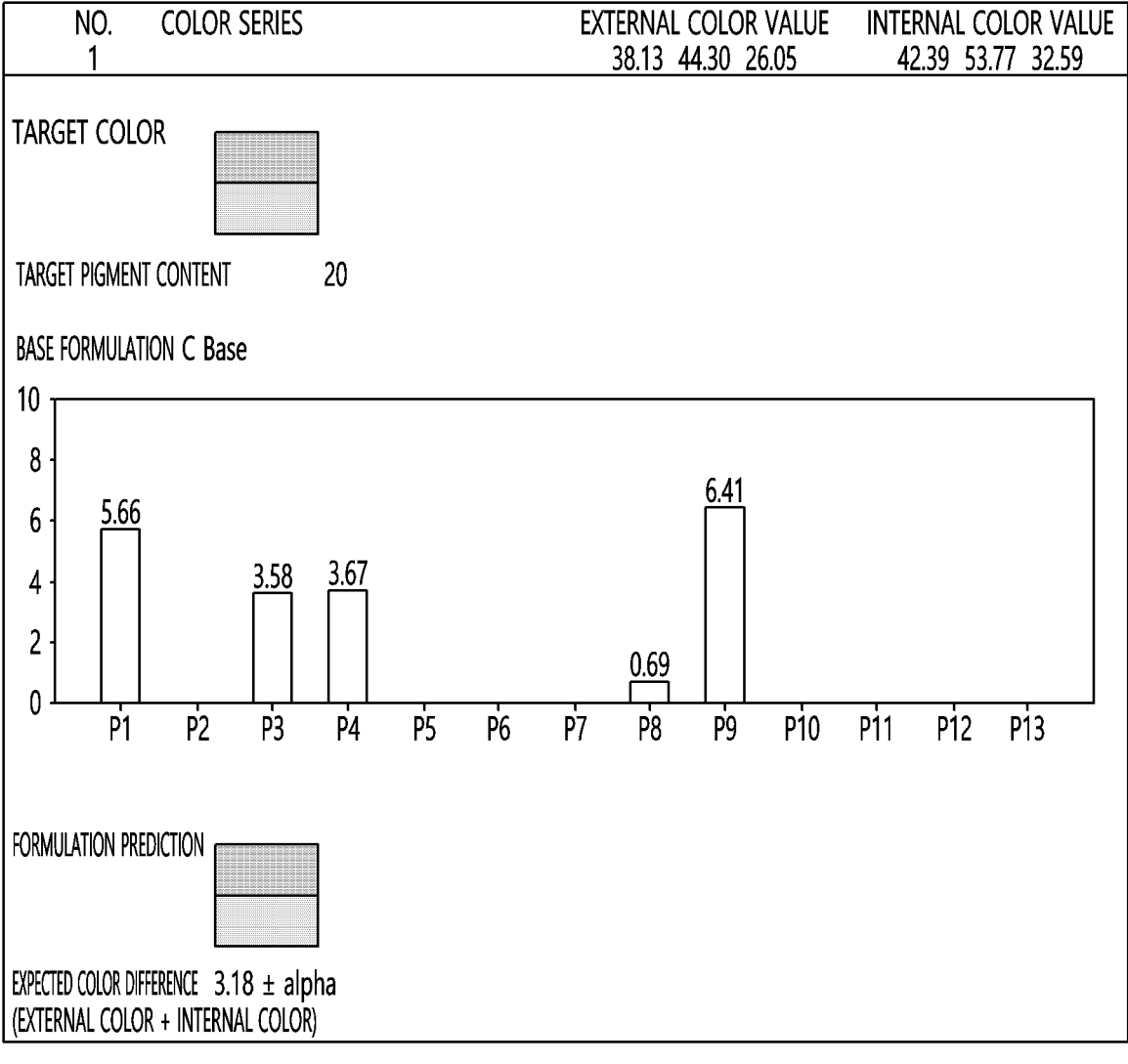
FIGS. 6 to 11 are diagrams illustrating examples for outputting a result formulation according to a target color for development by an apparatus for obtaining a raw material according to an embodiment of the present disclosure.

FIG. 6 is the example in which the predicted formulation having 5.66, 3.58, 3.67, 0.69, and 6.41 at the content of raw materials P1, P3, P4, P8, and P9, respectively, was derived when the apparatus for obtaining a raw material received 38.13, 44.30, 26.05, 42.39, 53.77, and 32.59 for the external color $L^*$, $a^*$, $b^*$ and the internal color $L^*$, $a^*$, $b^*$ as the target color for development. In addition, in this case, it was confirmed that the expected color according to the actual formulation is very similar to the target color according to the external color development value and the internal color development value.

Figure 7:
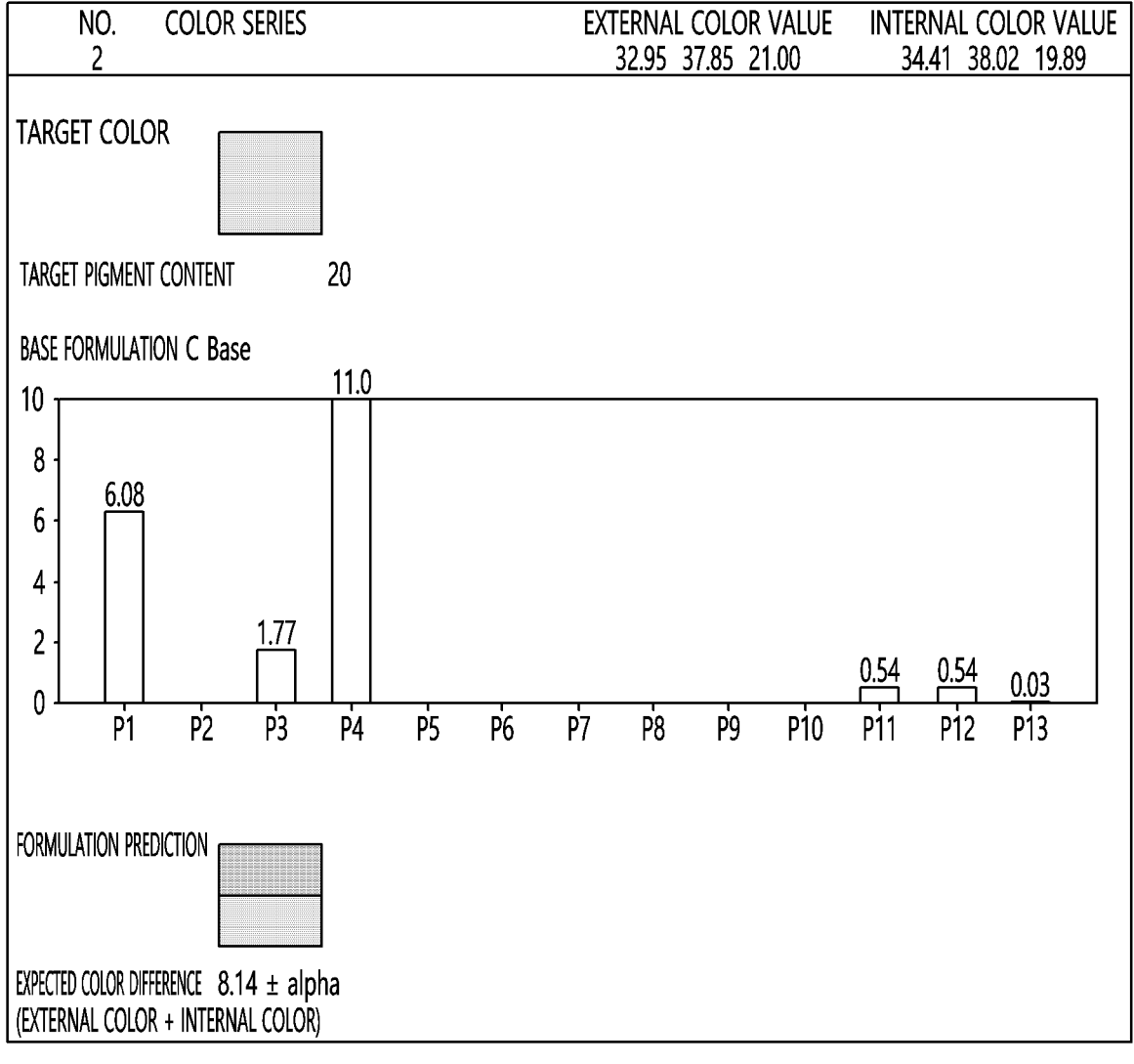

FIG. 7 is the example in which the predicted formulation having 6.08, 1.77, 11.0, 0.54, 0.54, and 0.03 at the content of raw materials P1, P3, P4, P11, P12, and P13, respectively, was derived when the apparatus for obtaining a raw material received 32.95, 37.85, 21.00, 34.41, 38.02, and 19.89 for the external color $L^*$, $a^*$, $b^*$ and the internal color $L^*$, $a^*$, $b^*$ as the target color for development. In addition, in this case, it was confirmed that the expected color according to the actual formulation is very similar to the target color according to the external color development value and the internal color development value.

Figure 8:
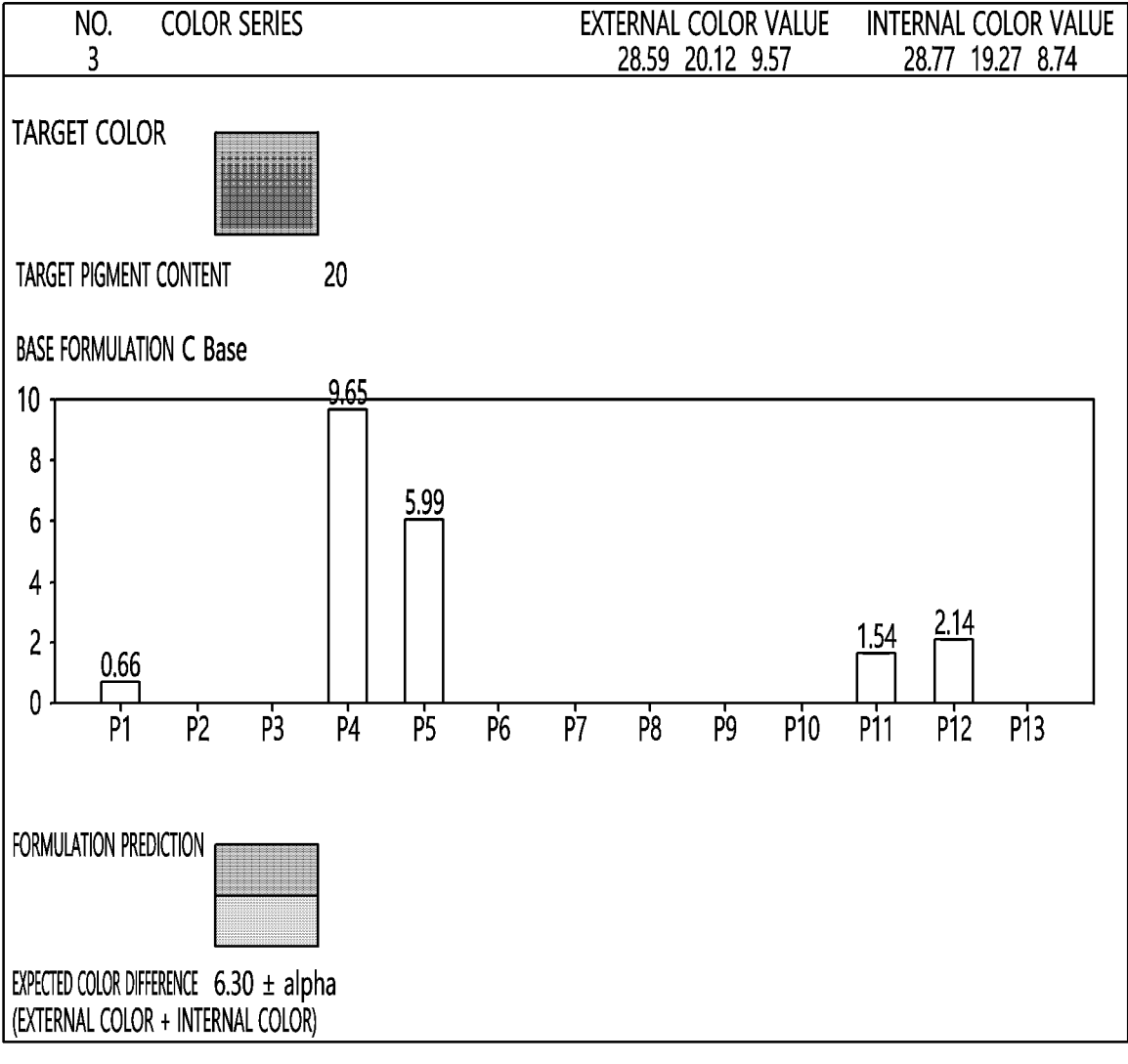

FIG. 8 is the example in which the predicted formulation having 0.66, 9.65, 5.99, 1.54, and 2.14 at the content of raw materials P1, P4, P5, P11, and P12, respectively, was derived when the apparatus for obtaining a raw material received 28.59, 20.12, 9.57, 28.77, 19.27, and 8.74 for the external color L*, a*, b* and the internal color L*, a*, b* as the target color for development. In addition, in this case, it was confirmed that the expected color according to the actual formulation is very similar to the target color according to the external color development value and the internal color development value.

Figure 9:
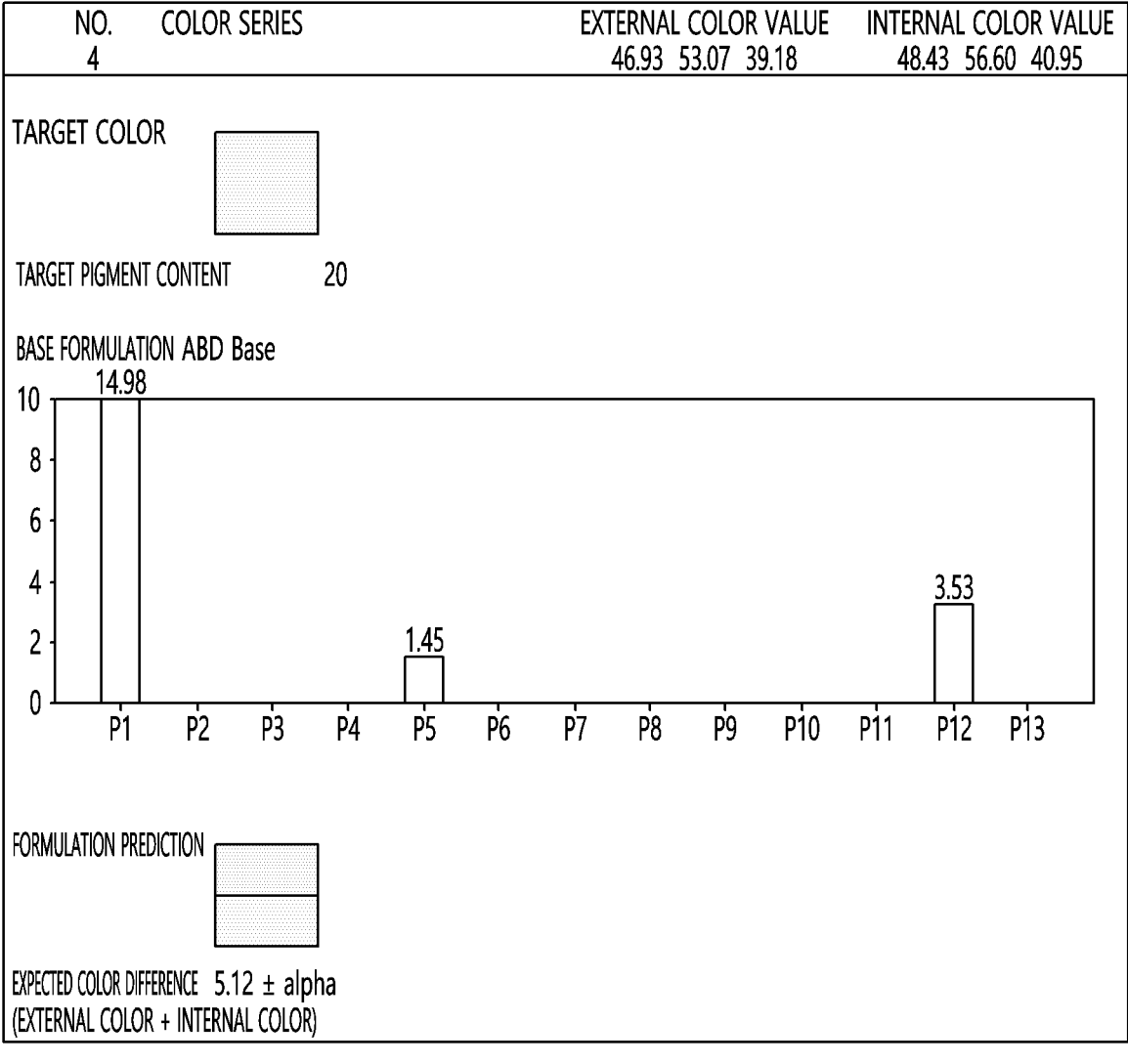

FIG. 9 is the example in which the predicted formulation having 10, 1.45, and 3.53 at the content of raw materials P1, P5, and P12, respectively, was derived when the apparatus for obtaining a raw material received 46.93, 53.07, 39.18, 48.43, 56.60, and 40.95 for the external color L*, a*, b* and the internal color L*, a*, b* as the target color for development. In addition, in this case, it was confirmed that the expected color according to the actual formulation is very similar to the target color according to the external color development value and the internal color development value.

Figure 10:
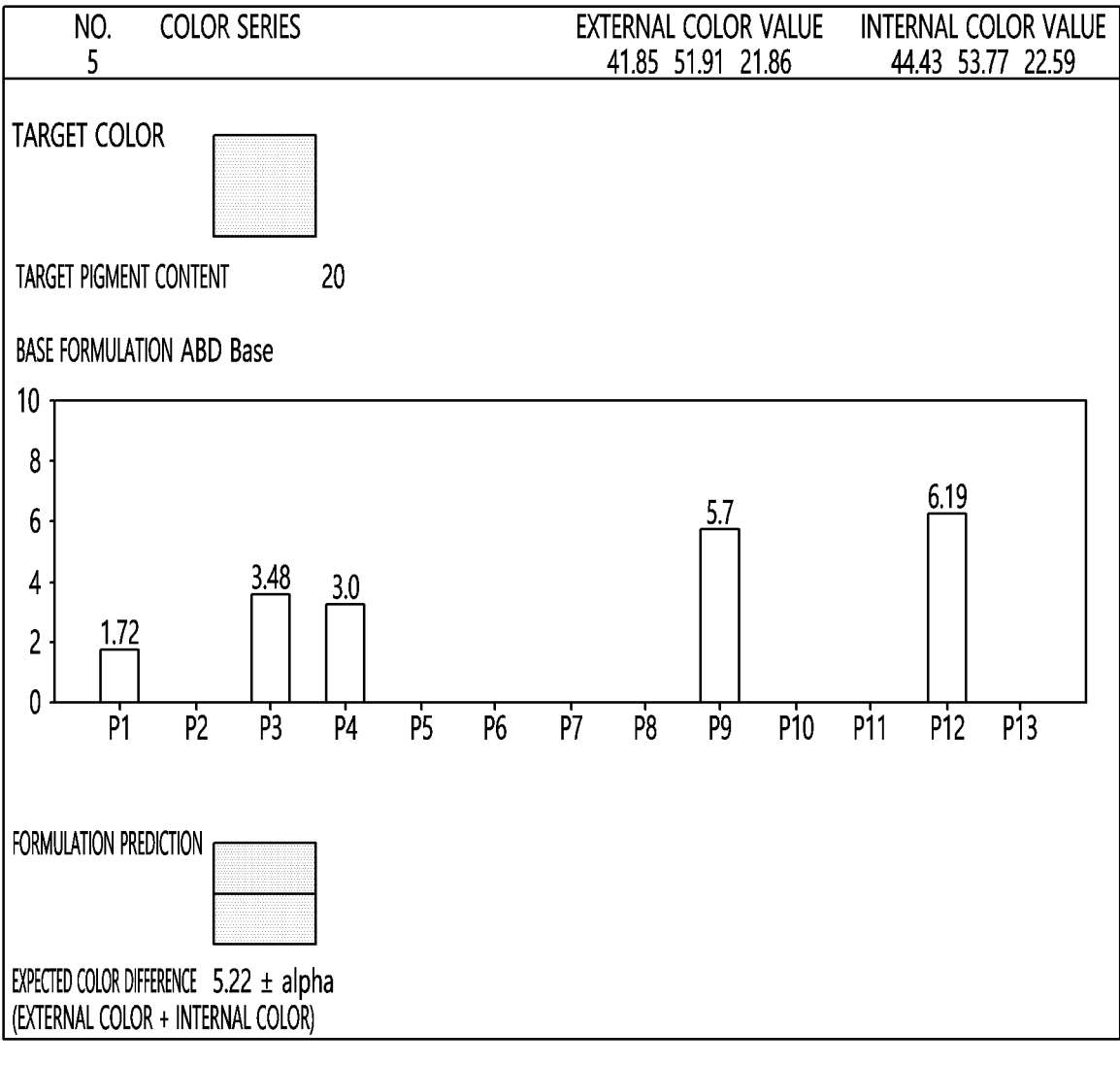

FIG. 10 is the example in which the predicted formulation having 1.72, 3.38, 3.0, 5.7, and 6.19 at the content of raw materials P1, P3, P4, P9, and P12, respectively, was derived when the apparatus for obtaining a raw material received 41.85, 51.91, 21.86, 44.43, 53.77, and 22.59 for the external color L*, a*, b* and the internal color L*, a*, b* as the target color for development. In addition, in this case, it was confirmed that the expected color according to the actual formulation is very similar to the target color according to the external color development value and the internal color development value.

Figure 11:
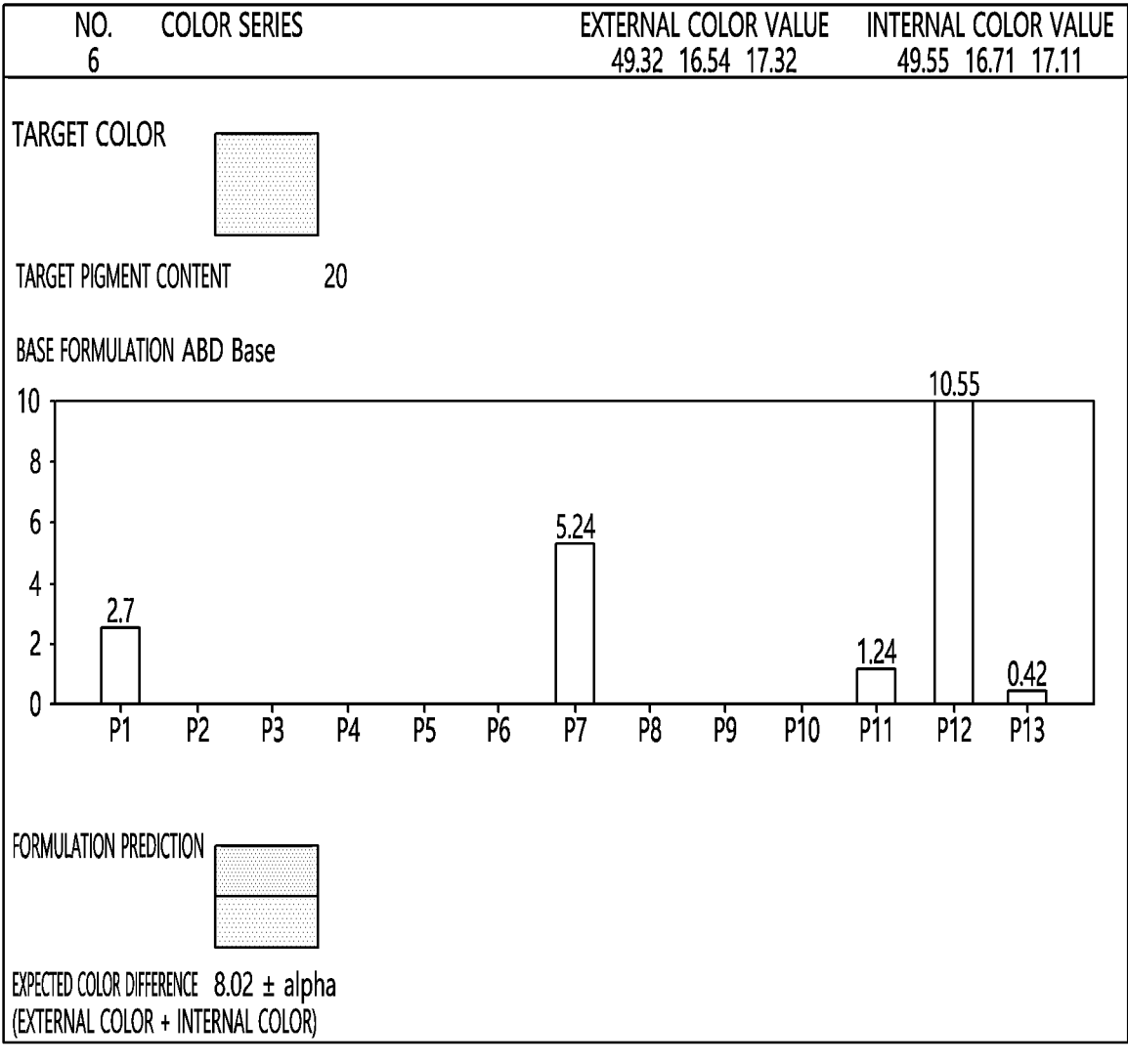

FIG. 11 is the example in which the predicted formulation having 2.7, 5.24, 1.24, 10.55, and 0.42 at the content of raw materials P1, P7, P11, P12, and P13, respectively, was derived when the apparatus for obtaining a raw material received 49.32, 16.54, 17.32, 49.55, 16.71, and 17.11 for the external color L*, a*, b* and the internal color L*, a*, b* as the target color for development. In addition, in this case, it was confirmed that the expected color according to the actual formulation is very similar to the target color according to the external color development value and the internal color development value.

Figure 12:
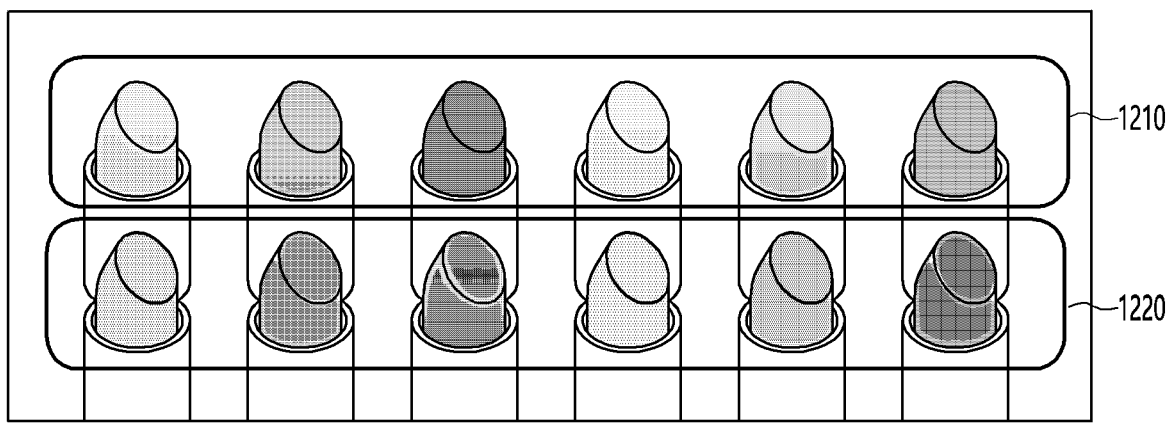
FIGS. 12 and 13 are pictures illustrating internal and external colors of color cosmetics using the result formulations derived from examples of FIGS. 6 to 11.
Figure 13:
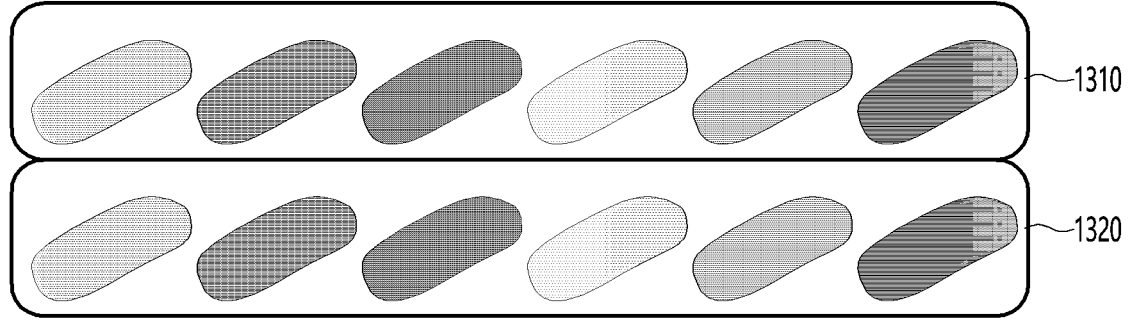

FIGS. 12 and 13 are the pictures illustrating the internal colors and the external colors of color cosmetics manufactured using the result formulations derived from examples of FIGS. 6 to 11.

Specifically, the external colors of cosmetics manufactured according to the result formulations are shown in the upper part 1210 of FIG. 12, and the external colors of the target color cosmetic products aimed to achieve through the apparatus for obtaining a raw material are shown in the lower part 1220 of FIG. 12.

In addition, the internal colors of the cosmetics manufactured according to the result formulations are shown in the upper part 1310 of FIG. 13, and the internal colors of the target color cosmetic products aimed to achieve through the apparatus for obtaining a raw material are shown in the lower part 1320 of FIG. 13.

In more detail, the average error of 4.6% for internal color and the average error of 6.4% for external color were measured, and it was confirmed that the apparatus for obtaining a raw material may more accurately derive a raw material for manufacturing cosmetics capable of developing the desired color.

The present disclosure described above may be implemented as computer-readable codes in a medium on which a program is recorded. The computer-readable medium includes all kinds of recording devices in which computer-readable data is stored. Examples of the computer-readable medium include a hard disk drive (HDD), a solid state disk (SSD), a silicon disk drive (SDD), a ROM, a RAM, a CD-ROM, a magnetic tape, a floppy disk, and an optical data storage, etc. In addition, the computer may include the apparatus for obtaining a raw material. Therefore, the above detailed description should not be construed in a limiting sense in all respects, and should be considered as examples. The scope of the present invention should be determined by rational interpretation of the appended claims, and encompasses all alterations falling within the equivalent scope of the appended claims.

The above description is merely illustrative of the technical spirit of the present invention, and various modifications and variations will be possible without departing from the essential characteristics of the present invention by those skilled in the art to which the present invention pertains.

Therefore, the embodiments disclosed in the present invention are not intended to limit the technical spirit of the present invention, but to explain, and the scope of the technical spirit of the present invention is not limited by these embodiments.

The protection scope of the present invention should be construed by the following claims, and all technical ideas within the equivalent range should be construed as being included in the scope of the present invention.

The invention claimed is:

1. An apparatus for obtaining a raw material comprising:
an input unit for receiving a target color for development;
a formulation sample group generation unit for generating a formulation sample group according to the target color for development;
a formulation sample improvement unit for outputting the formulation sample group as an improved sample group using a genetic algorithm; and
an improved sample group convergence checking unit for outputting the improved sample group to the formulation sample improvement unit or an output unit according to whether all samples in the improved sample group converge to a preset reference range,
wherein the output unit outputs raw material information for manufacturing color cosmetics having the target color for development based on the improved sample group output from the formulation sample improvement unit,
the raw material information includes a content of at least one raw material, and
the formulation sample improvement unit includes
a sample candidate derivation unit for generating a combination sample by selecting any one of existing samples and any one of the remaining existing samples as a random sample, mutating the random sample into a mutation sample by performing interpolation to select a value between a content contained in the selected existing sample and a content contained in the random sample, and then combining the mutation sample with the one of the existing samples,
a sample evaluation unit for calculating the first color difference between a predicted color development value of the selected existing sample and the target color for development and the second color difference between a predicted color development value of the combination sample and the target color for development, and a sample selection unit for outputting the sample having the smaller value among the first and the second color differences as an improved sample in the improved sample group.

2. The apparatus for obtaining a raw material of claim 1, wherein the input unit further receives an option item, and the formulation sample improvement unit outputs the raw material information by reflecting the option item.

3. The apparatus for obtaining a raw material of claim 2, wherein the option item includes at least one of the maximum number of raw materials, a range of content ratio for each raw material, and a total raw material content.

4. The apparatus for obtaining a raw material of claim 1, wherein when there is an option item, the formulation sample improvement unit compares the first color difference on which a penalty according to the option item is reflected with the second color difference on which a penalty according to the option item is reflected.

5. The apparatus for obtaining a raw material of claim 1, wherein the improved sample group convergence checking unit determines that all samples in the improved sample group converge to the preset reference range when a variance of content for each raw material in the improved sample group is less than a preset reference value.

6. The apparatus for obtaining a raw material of claim 5, wherein the improved sample group convergence checking unit outputs the improved sample group to the output unit when determining that all samples in the improved sample group converge to the preset reference range.

7. The apparatus for obtaining a raw material of claim 5, wherein the improved sample group convergence checking unit outputs the improved sample group to the formulation sample improvement unit when determining that all samples in the improved sample group do not converge to the preset reference range.

8. The apparatus for obtaining a raw material of claim 7, wherein the formulation sample improvement unit outputs a secondary improved sample group for the improved sample group input from the sample group convergence checking unit.

9. The apparatus for obtaining a raw material of claim 1, wherein the formulation sample improvement unit randomly selects any one value of the existing sample and the mutation sample to generate the combination sample.

10. The apparatus for obtaining a raw material of claim 1, further comprising a color development prediction calculation unit for calculating the predicted color development of the existing sample and the predicted color development of the combination sample through a regression model.

11. The apparatus for obtaining a raw material of claim 10, further comprising a color development prediction model generation unit for generating a regression model by using color development data according to formulation data, wherein the color development prediction calculation unit outputs a predicted color development value calculated through the regression model when a predicted formulation value is input, the formulation data is color raw material information on previously manufactured color cosmetics, and the color development data is color value corresponding to the color cosmetics.

12. The apparatus for obtaining a raw material of claim 11, further comprising a predicted formulation generation unit configured to receive the target color for development, transmit a predicted formulation value generated according to the target color for development to the color development prediction calculation unit, and receive the predicted color development value corresponding to the predicted formulation value from the color development prediction calculation unit.

13. The apparatus for obtaining a raw material of claim 12, wherein the predicted formulation generation unit improves the predicted formulation value until a color difference between the predicted color development value and the target color for development converges within a preset reference range.

14. The apparatus for obtaining a raw material of claim 13, wherein the one of the existing samples or the random sample include information on at least one raw material and a content of the raw material, and
the sample candidate derivation unit performs the interpolation by selecting any one of values between a content of the raw material contained in the selected existing samples and a content of the corresponding raw material contained in the random sample.

15. A method of obtaining a raw material comprising:
receiving a target color for development;
generating a formulation sample group according to the target color for development;
outputting the formulation sample group as an improved sample group using a genetic algorithm;
obtaining whether all samples in the improved sample group converge to a preset reference range; and
outputting raw material information or outputting a secondary improved sample group for the improved sample group according to whether all samples in the improved sample group converge to the preset reference range,
wherein the outputting of the formulation sample group as the improved sample group includes:
generating a combination sample by selecting any one of the existing samples and any one of the remaining existing samples as a random sample, mutating the random sample into a mutation sample by performing interpolation to select a value between a content contained in the selected existing sample and a content contained in the random sample, and then combining the mutation sample with the selected existing sample;
calculating the first color difference between a predicted color development value of the selected existing sample and the target color for development and the second color difference between a predicted color development value of the combination sample and the target color for development; and
outputting the sample having the smaller value among the first and second color differences as an improved sample in the improved sample group, and
wherein the outputting of the raw material information is outputting the raw material information for manufacturing color cosmetics having the target color for development based on the improved sample group output from the formulation sample improvement unit.

16. The method of obtaining a raw material of claim 15, further comprising receiving an option item,
wherein the outputting of the raw material information is outputting the raw material information by reflecting the option item.

17. The method of obtaining a raw material of claim 16, wherein the receiving of the option item is receiving at least one of the maximum number of raw materials, a range of content ratio for each raw material, and a total raw material content.

18. The method of obtaining a raw material of claim 15, wherein the outputting of the formulation sample group as the improved sample group includes comparing the first color difference on which a penalty according to the option item is reflected with the second color difference on which a penalty according to the option item is reflected.

19. The method of obtaining a raw material of claim 15, wherein the obtaining of whether all samples in the improved sample group converge to the preset reference range is determining that when a variance of content for each raw material in the improved sample group is less than a preset reference value, all samples in the improved sample group converge thereto.

20. The method of obtaining a raw material of claim 15, wherein the generating of the combination sample is generating the combination sample by randomly selecting any one value of the existing samples and the mutation sample.

\* \* \* \* \*